(12) United States Patent
Steele (10) Patent No.: US 9,423,062 B2
(45) Date of Patent: Aug. 23, 2016

(54) TWIST LOCK CONNECTOR WITH REINFORCING WING GRIPS AND REVERSE SNAP ASSEMBLY

(71) Applicant: Nordson Corporation, Westlake, OH (US)

(72) Inventor: Kyle R. Steele, Fort Collins, CO (US)

(73) Assignee: Nordson Corporation, Westlake, OH (US)

( * ) Notice: Subject to any disclaimer, the term of this patent is extended or adjusted under 35 U.S.C. 154(b) by 413 days.

(21) Appl. No.: 13/826,568

(22) Filed: Mar. 14, 2013

(65) Prior Publication Data
US 2013/0320672 A1   Dec. 5, 2013

Related U.S. Application Data

(60) Provisional application No. 61/653,867, filed on May 31, 2012.

(51) Int. Cl.
  *F16L 37/24*  (2006.01)
  *F16L 37/098*  (2006.01)
  (Continued)

(52) U.S. Cl.
  CPC ........ *F16L 37/0982* (2013.01); *A61M 39/1011* (2013.01); *F16L 37/107* (2013.01); *F16L 37/248* (2013.01); *A61M 2039/1027* (2013.01); *A61M 2039/1033* (2013.01)

(58) Field of Classification Search
  CPC ................. Y10T 24/44026; Y10T 24/309
  USPC ........................................................ 403/326
  See application file for complete search history.

(56) References Cited

U.S. PATENT DOCUMENTS 380,363 A * 4/1888 Sturgeon ........................ 285/70
768,359 A * 8/1904 Eisenhuth ..................... 285/362
(Continued)

FOREIGN PATENT DOCUMENTS

CN   102186334 A   9/2011
CN   202746822 U   2/2013
(Continued)

OTHER PUBLICATIONS

CPC—Colder Products Company, www.colder.com—"SMC02 1/8 Hose Barb Non-Valved in-Line Coupling Set", http://www.colder.com/Tabid/72/MaterialiD/1/ciD/1/siD/5/tiD/1/piD/173/Products.aspx. Retrieved from the Internet on Jul. 14, 2014, (Applicant believes that information similar to that presented in this document was available on this website at least as early as the priority date), 1 page.
(Continued)

*Primary Examiner* — Daniel P Stodola
*Assistant Examiner* — James Linford
(74) *Attorney, Agent, or Firm* — Baker & Hostetler LLP (57) ABSTRACT

A connector assembly may be formed by the combination of a latch member and a connector member. The latch member has an annular collar and an arcuate latch wall extending from a circumferential edge of the annular collar. A latch recess and a latch arm are defined within the latch wall. A wing grip extends from an exterior surface of the latch wall adjacent the latch recess and is configured to reinforce the latch arm by countering a tendency of the latch arm to flex radially outward when the connector assembly is subject to a tension load along a longitudinal axis of the connector assembly. A plurality of snap arms are arranged about a circumference of the interior surface of the annular collar to engage the connector member. The connector member receives and retains the latch member directly about an outer male insertion surface thereof rather than passing a barbed end of the connector member through the latch member. The latch member and the connector member are correspondingly configured to freely rotate relative to one another upon assembly. An annular protrusion on an outer wall of the connector member acts as a tube stop.

19 Claims, 9 Drawing Sheets

(51) Int. Cl.
*F16L 37/248* (2006.01)
*F16L 37/107* (2006.01)
*A61M 39/10* (2006.01)

(56) References Cited

U.S. PATENT DOCUMENTS

| | | | |
|---|---|---|---|
| 770,049 A * | 9/1904 | Dorgans | 285/70 |
| 2,240,330 A * | 4/1941 | Flagg et al. | 606/225 |
| 3,203,714 A | 8/1965 | Cronk et al. | |
| 3,245,703 A | 4/1966 | Manly | |
| D254,505 S | 3/1980 | Parsons et al. | |
| D265,418 S | 7/1982 | Chow et al. | |
| D275,316 S | 8/1984 | Hayes | |
| 4,541,657 A | 9/1985 | Smyth | |
| 4,770,445 A * | 9/1988 | Steer | A61F 5/4405 285/110 |
| 4,793,637 A | 12/1988 | Laipply et al. | |
| D327,120 S | 6/1992 | Ambrosi | |
| D345,962 S | 4/1994 | Clifton et al. | |
| D366,866 S | 2/1996 | Whitehead et al. | |
| D379,348 S | 5/1997 | Korinek | |
| 5,799,987 A | 9/1998 | Sampson | |
| D402,629 S | 12/1998 | Benedict | |
| D404,714 S | 1/1999 | Axelsson | |
| 6,062,763 A * | 5/2000 | Sirois et al. | 403/329 |
| 6,252,170 B1 | 6/2001 | Korinek | |
| D495,050 S | 8/2004 | Guala | |
| D523,821 S | 6/2006 | Michaud et al. | |
| D569,955 S | 5/2008 | Chen | |
| D570,457 S | 6/2008 | Brown | |
| D613,827 S | 4/2010 | Damaske et al. | |
| D630,320 S | 1/2011 | Lombardi, III et al. | |
| D645,547 S | 9/2011 | Lombardi et al. | |
| D651,696 S | 1/2012 | Giordano | |
| 2003/0085571 A1 * | 5/2003 | Avery | 285/361 |
| 2008/0129047 A1 | 6/2008 | Blivet et al. | |
| 2011/0193342 A1 | 8/2011 | Hoefelmayr | |
| 2012/0006419 A1 * | 1/2012 | Richardson | A62C 33/00 137/15.01 |
| 2013/0048133 A1 | 2/2013 | Richardson | |

FOREIGN PATENT DOCUMENTS

FR 1238369 * 8/1960
GB 456875 A 11/1936

OTHER PUBLICATIONS

CPC—Colder Products Company, www.colder.com—"SMMP Male Plug for SMC Series Coupling Bodies", https://www.colder.com/Tabid/72/MaterialiD/1/cID/1/sID/5/tID/15/pID/5285/Products.aspx; Retrieved from the Internet on Oct. 13, 2014, (Applicant believes that information similar to that presented in this document was available on this website at least as early as the priority date), 1 page.

CPC—Colder Products Company, www.colder.com search results for "SMC", http://www.colder.com/SearchResults.aspx?Search=smc, Retrieved from the Internet on Jul. 14, 2014, (Applicant believes that information similar to that presented in this document was available on this website at least as early as the priority date), 3 pages.

Chinese Application No. 201310215062.x: First Office Action dated Feb. 22, 2016, 12 pages.

* cited by examiner

TWIST LOCK CONNECTOR WITH REINFORCING WING GRIPS AND REVERSE SNAP ASSEMBLY

CROSS REFERENCE TO RELATED APPLICATIONS

This application claims the benefit of priority pursuant to 35 U.S.C. §119(e) of U.S. provisional application No. 61/653,867 filed 31 May 2012 entitled "Twist lock connector with reinforcing wing grips and reverse snap assembly," which is hereby incorporated herein by reference in its entirety

BACKGROUND

Various fluid tubing connectors may be used in limb cuff applications. These components are primarily used in blood pressure applications, which means they typically transport a gas (generally air) over a range of pressures. Such connectors are generally configured with opposing connector ends. One connector end may be configured to join with tubing extending from a blood pressure cuff, while the opposing connector end is configured to join with tubing extending from the blood pressure measurement device. Typically the connector ends are configured with a "quarter turn" latch design in which engagement features on each connector end lock together upon 90° rotation with respect to each other. In some designs, the connectors may be configured to form a unitary piece with no moving parts, in which case the respective tubing extending from the blood pressure cuff and the blood pressure measurement device are prevented from rotating relative to one another. This may be problematic in cases where an axial tension load is exerted on the connector or the components joined thereto as this may result in folding or crimping of the tubing, which may affect blood pressure readings, or complete detachment of the connector halves.

Some connectors may be configured as two-piece connectors that may include a connector member and a cylindrical shroud or collar member, which are rotatable relative to one another. In some two-piece connector designs, the connector member may be configured with a barb connector portion that may be used to join with tubing extending from a blood pressure cuff or a blood pressure measurement device, and the collar member of the two-piece connector may be configured with threads or a latch that may join to the tubing extending from the other of the blood pressure cuff or the blood pressure device. Typically, two-piece connectors are assembled by passing the barb connector portion through the collar member until the collar member engages in a snap fit position on the collar member. Due to this direction of assembly, the barb connector portion of the connector member requires an outer circumference that is smaller than an inner circumference of the collar member, which means that only certain tubing sizes may be used with the barb connector portion of the two-piece connector.

While the collar member and the connector member of the two-piece connector may rotate relative to one another when assembled, free rotation of the components of the two-piece connector may be impeded. For example, when tubing is joined to the barb connector member, the tubing may extend along the length of the barb connector member up to and over the collar member, thereby impeding rotation of the collar member. Where a tube stop is provided on the barb connector portion of the connector member, the tube stop requires an outer circumference that is smaller than an inner circumference of the collar member to enable assembly of the two-piece connector.

In addition, in typical two-piece connector designs, the collar member may include an engagement hook or slot with a retention bump configured to engage with a corresponding hook or slot with a retention bump on the opposing connection member engagement joined to tubing extending from the blood pressure device upon the quarter turn rotation. When subject to an axial tension load, the engagement hook of the collar member may flex radially outwardly and slide past and disengage from the engagement hook of the connection member joined to tubing extending from the blood pressure measurement device. In other instances, a high axial tension can cause one of the engagement hooks to fail, e.g., by shearing off, thereby causing the opposing connection members to disengage.

The information included in this Background section of the specification, including any references cited herein and any description or discussion thereof, is included for technical reference purposes only and is not to be regarded subject matter by which the scope of the invention is to be bound.

SUMMARY

One exemplary implementation of a connector assembly may be formed by the combination of a latch member and a connector member. The latch member may have an annular collar and an arcuate latch wall extending from a circumferential edge of the annular collar. A latch recess and a latch arm may be defined within the latch wall. A wing grip may extend from an exterior surface of the latch wall adjacent the latch recess and may be configured to reinforce the latch arm by countering a tendency of the latch arm to flex radially outward when the connector assembly is subject to a tension load along a longitudinal axis of the connector assembly. The connector member may be configured to receive and retain the latch member about an outer surface thereof. The latch member and the connector member may be correspondingly configured to freely rotate relative to one another upon assembly.

Another exemplary implementation of a connector assembly may be formed by the combination of a latch member and a connector member. The latch member may have an annular collar with a first open end and an opposing second open end and a snap assembly. The snap assembly may be provided on an interior surface of the annular collar adjacent the first open end. The snap assembly may have a plurality of snap arms arranged about a circumference of the interior surface of the annular collar. Each of the snaps arms may be configured with a free end extending at an angle toward both a longitudinal axis of the annular collar and the second open end. The connector member may have a first end for attachment to a length of fluid tubing and a second end for connection with a complementary connector member. The connector member may have lumen defined by an internal wall of the connector member extending between the first end and the second end along a longitudinal axis of the connector assembly. The connector member may further have an engagement portion located adjacent the second end separated from the first end by an annular protrusion on an outer wall of the connector member. The annular protrusion may have a diameter that is larger than a diameter of the first open end of the annular collar. The latch member may be rotatably connected with the connector member by insertion of the second end of the connector member into the first open end of the annular collar of the latch member until the first open end of the annular collar abuts the annular protrusion. In the assembled position, the snap assembly of the latch member may retain the latch member about the engagement portion of the connector member.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

DETAILED DESCRIPTION

The following description highlights several improved features for incorporation into twist lock connector assemblies configured to join two or more components, such as tubing from a limb pressure cuff and a blood pressure measurement device. For best functionality of a twist lock connector for blood pressure applications, the latch mechanism, which is typically in the form of an annular collar mounted about a male insert connector, should be able to be rotated both clockwise and counterclockwise with respect to the longitudinal axis through the flow path of the connector assembly. Because of this desire for rotation, the "grip" of the latch collar should be adequate for a user to be able to rotate and disengage or engage the latch collar without slippage occurring between the fingers of the user and the outer surfaces of the component. Since the overall diameter of these components is small, the addition of protruding wing grips may aid in the ergonomics as well as overall functionality of the latch mechanism. Without wing grips, the user may have to exert a significant amount of force onto the wing grip to not slip during rotation. With wing grips, the force required to actuate the latch mechanism is significantly reduced. This helps people with arthritis or wet, gloved hands to connect and disconnect the latch.

The strength of the latch structure is also improved with the addition of protruding wing grips when placed in a strategic location. During an axial tension load, a typical latch structure on the collar-shaped latch flares radially outward. Ultimately, with a high enough load, opposing latch structures often either disengage or shear off, depending on the material of the component. When a wing grip is placed next to a latch arm as disclosed herein, the wing grip may counter the outward radial flexion of the latch arm and instead cause inward radial flexion when a tensile load is applied. The inward rotation causes the latch arm to essentially "dig in" to the opposing latch geometry, which prevents disengagement, generally leaving only material failure as a remaining possibility for latch failure, which is ultimately a stronger design.

The typical direction of assembly for the rotatable latch collar onto the male connector insert on most other connectors similar to the presently disclosed design is from the barb side of the connector, i.e., the latch collar is pushed over the barbed end to reach its engagement position on the male connector insert adjacent the insertion end. This generally is a good design choice to resist axial load forces; however, there are also drawbacks to this design choice. When the latch collar is assembled over the barb, the barb size is limited since the barb must pass through the inner diameter of the latch collar. Also when assembled over the barb, the shroud becomes the tube stop. When tubing is pressed all the way up to the shroud, the friction between the tubing and the shroud prevent the connector from freely rotating. Because of this, the tubing cannot be pressed all the way over the barb, thus not utilizing the full strength of the barb and making assembly difficult.

When the design is reversed as present in the present disclosure, i.e., where the latch collar is pushed over the sealing portion of the male connector insert toward the barb, several benefits over prior designs are gained. A first improvement is that the outer diameter of the barbed end of the male connector insert can be made as large as desired and can further take on any form for tubing connection as desired. A second benefit is that the latch connector may be assured of full and free rotation when the latch collar is assembled from the sealing side of the male connector insert. In the design disclosed herein, an annular ring on the male connector insert may provide a structure that acts both as a latch collar stop to prevent the latch collar from sliding over the barbed end and as a tube stop to prevent the tubing connected to the barbed end from interfering with the latch collar. The tubing can be pressed over the entire length of the barb and still not make contact with the latch collar. Further, as described above, the wing grips strengthen the latch arms of the latch collar and provide adequate resistance to axial tension to prevent disengagement of the male connector insert from a corresponding female connector.

Figure 1:
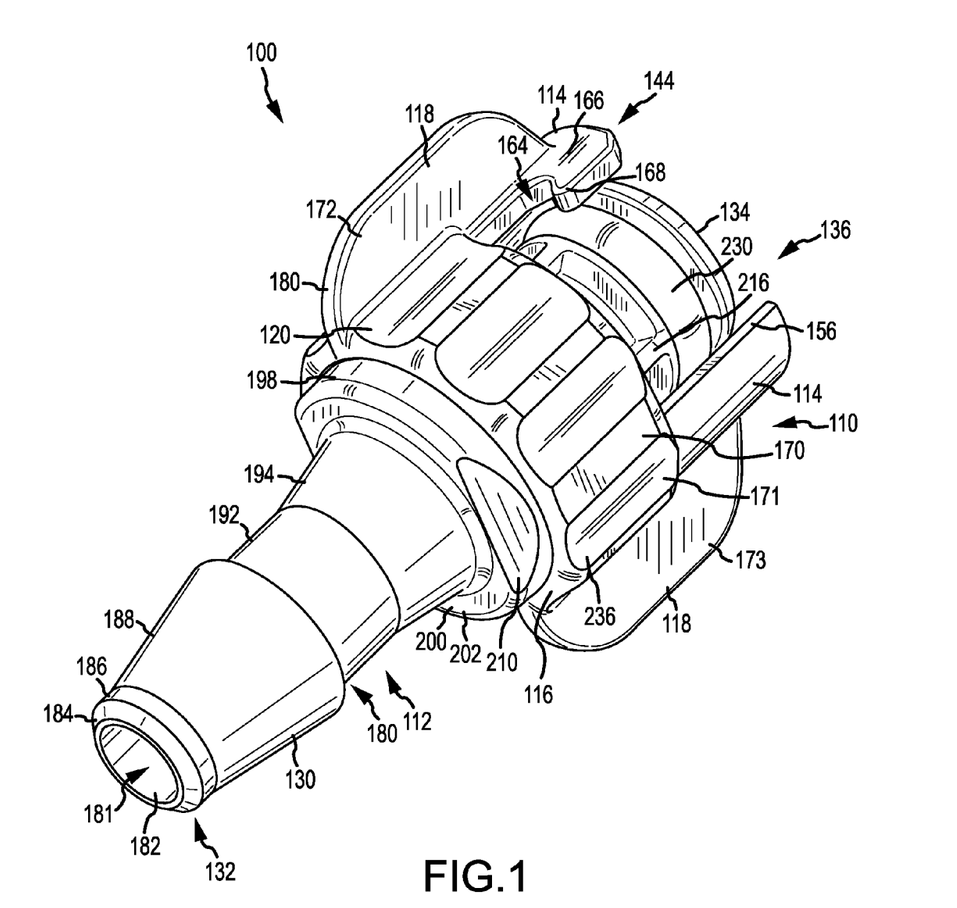
FIG. 1 is an isometric view of an exemplary implementation of a twist lock connector assembly.
Figure 2:
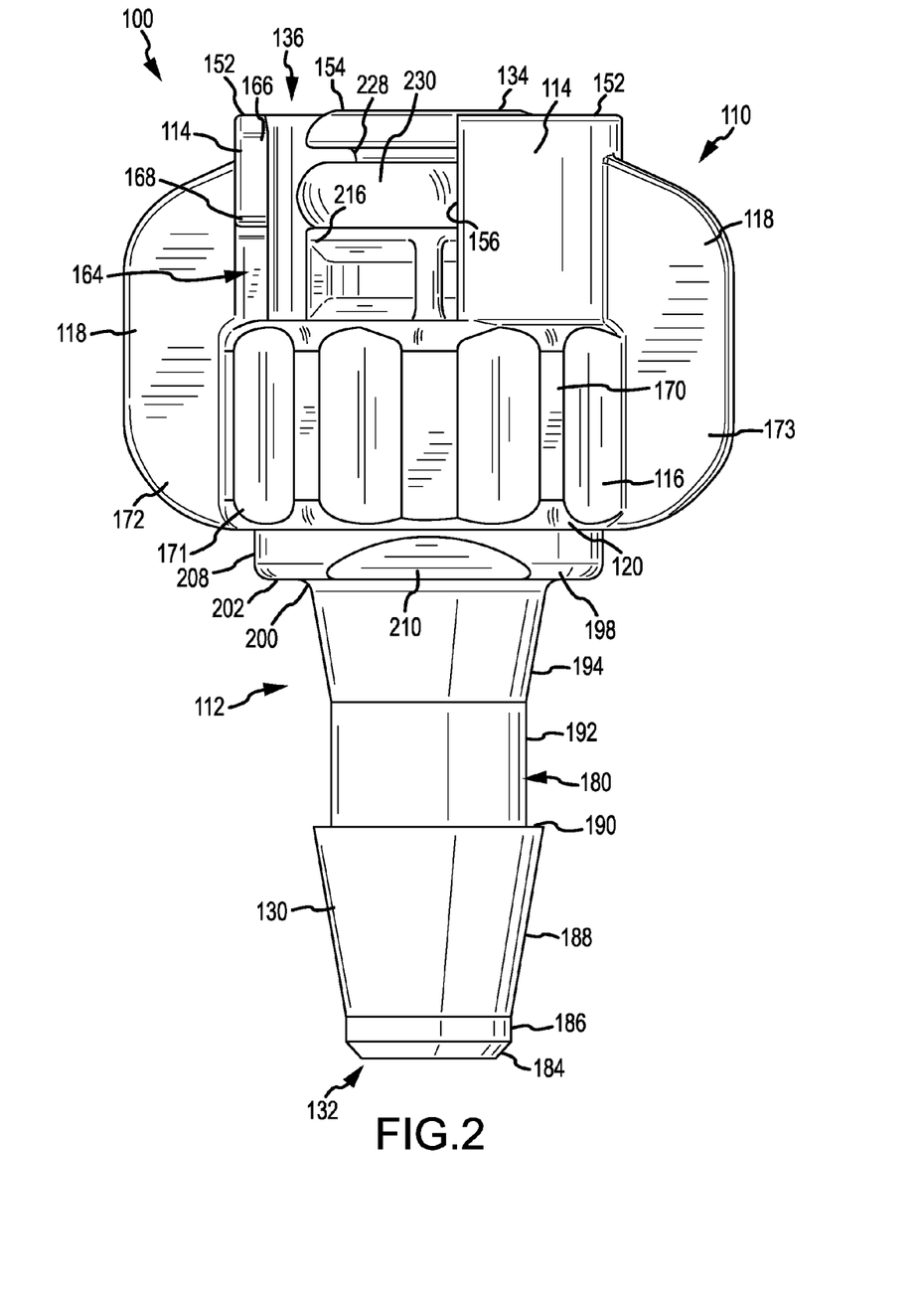
FIG. 2 is a side elevation view of the connector assembly of FIG. 1.

FIG. 1 depicts an exemplary implementation of a twist lock connector assembly 100 composed of two components: a generally cylindrical rotatable latch member 110 and a tubular male connector member 112 defining a lumen for fluid flow therethrough. The rotatable latch member 110 and connector member 112 may be freely rotatable relative to one another about the longitudinal axis of the connector assembly 100 in the assembled position of FIG. 1. In some implementations, the components of the connector assembly 100 may be substantially permanently joined to one another once in the assembled position, while in other implementations, the components of the connector assembly 100 may be releasably detachable from one another in the assembled position.

As depicted in FIGS. 1-6, the rotatable latch member 110 of the twist lock connector assembly 100 may be composed of four main components: arcuate latch walls 114, a annular collar 116, wing grips 118 extending normally from an exterior surface 120 of the annular collar 116, and a snap assembly 122 composed of snap arms 124 arranged about an interior surface 121 of the annular collar 116. The connector member 112 of the connector assembly 100 may be configured with three main components as shown in FIGS. 1-4 and 7; a barb connector portion 130 at a first or barb end 132, a male connector portion 134 at a second or male end 136, and a latch member engagement portion 138 arranged between the first and second ends 132, 136. In certain implementations, the snap arms 124 of the latch member 110 may be configured to be received in an annular channel 140 defined within the latch member engagement portion 138 on the outer wall of the connector member 112.

When the latch member 110 and connector member 112 are engaged with each other, they may freely rotate with respect to each other about the longitudinal axis of the connector assembly 100, while simultaneously restraining longitudinal movement of the latch member 110 with respect to the connector member 112 as described further below. Relative rotation of the latch member 110 and the connector member 112 may be facilitated by use of the wing grips 118 of the latch member 110. The wing grips 118 may be configured to receive rotational forces exerted by a user's fingers to enable engagement and disengagement of a latching mechanism 144 of the rotatable latch member 110, while adding strength to the latch member 100, described further below. The wing grips 118 may also facilitate use of the connector assembly 100 by those with arthritis or wet slippery hands.

The rotatable latch member 110 may be sized and configured with an internal diameter that enables the connector member 112 to be joined to the latch member 110 by inserting the male connector portion 134 of the connector member 112 into the latch member 110 through a first open end 148.

Figure 5A:
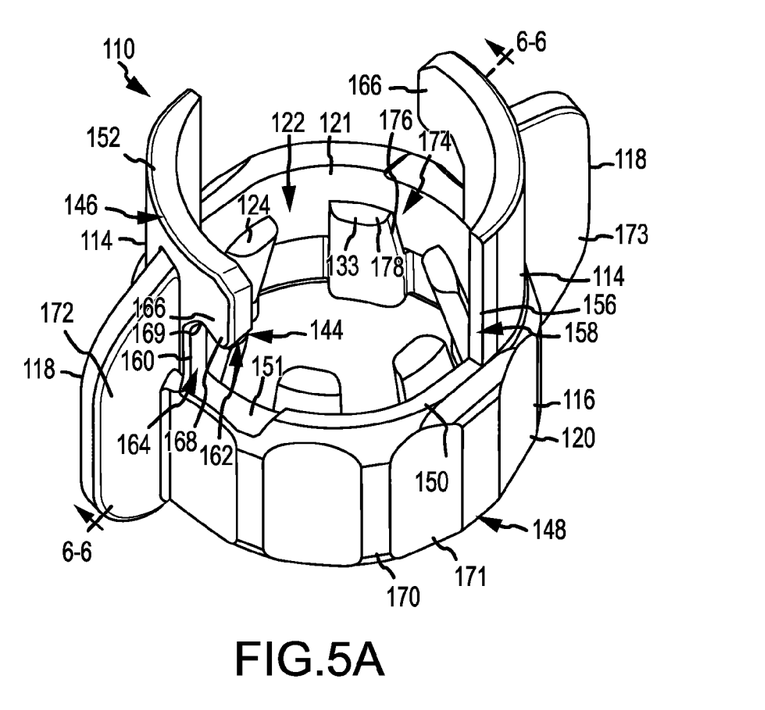
FIG. 5A is an isometric view of a rotatable latch member of the connector assembly of FIG. 1.
Figure 5B:
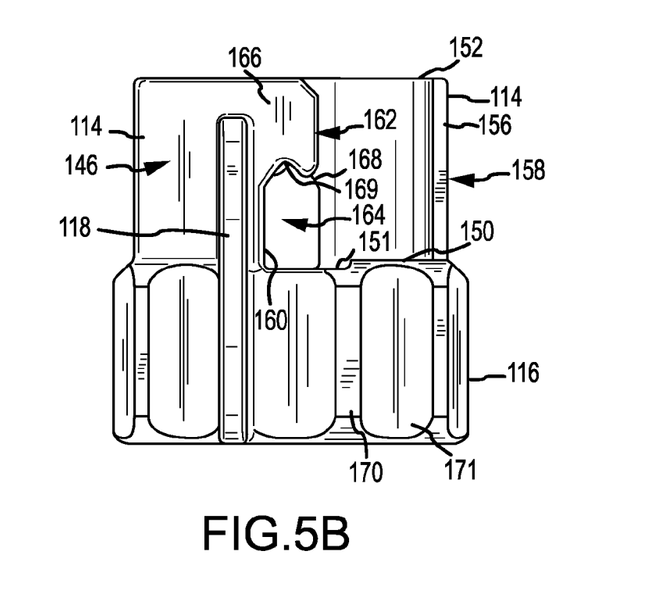
FIG. 5B is a side elevation view of the rotatable latch member of FIG. 5A.
Figure 6:
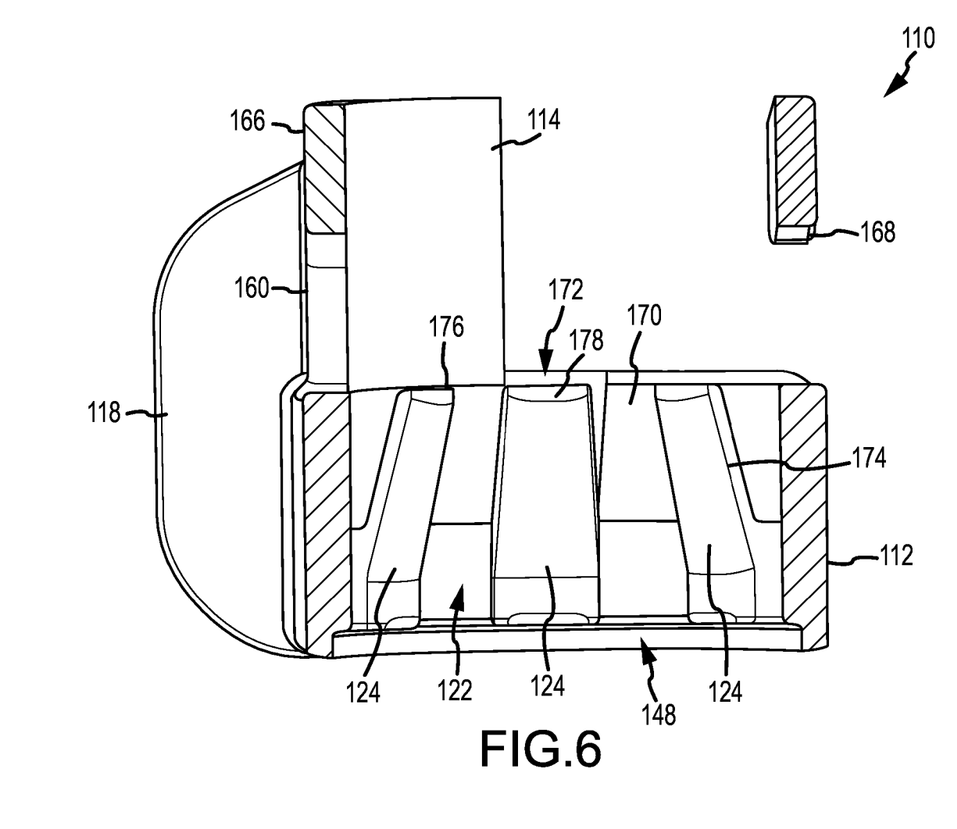
FIG. 6 is a cross-section view of the rotatable latch member of FIG. 5 taken along the line 6-6 as shown in FIG. 5.
Figure 7:
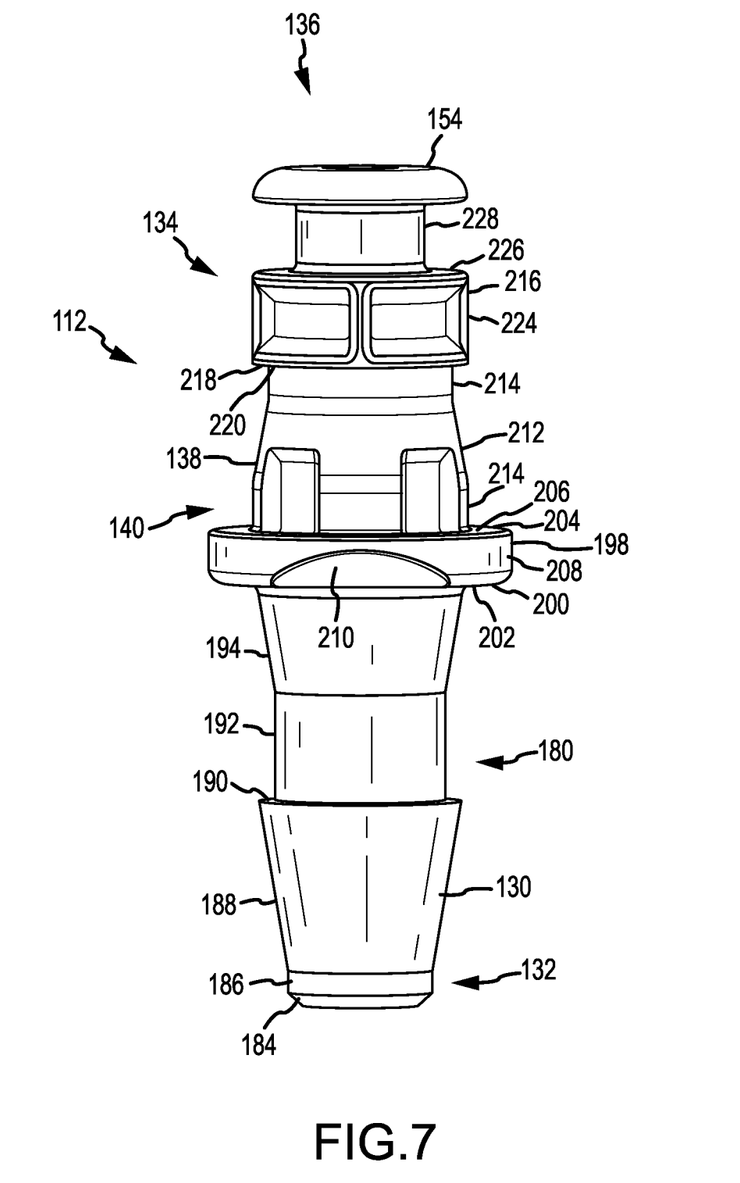
FIG. 7 is a side elevation view of a male fluid tubing connector member of the connector assembly of FIG. 1.
Figure 8:
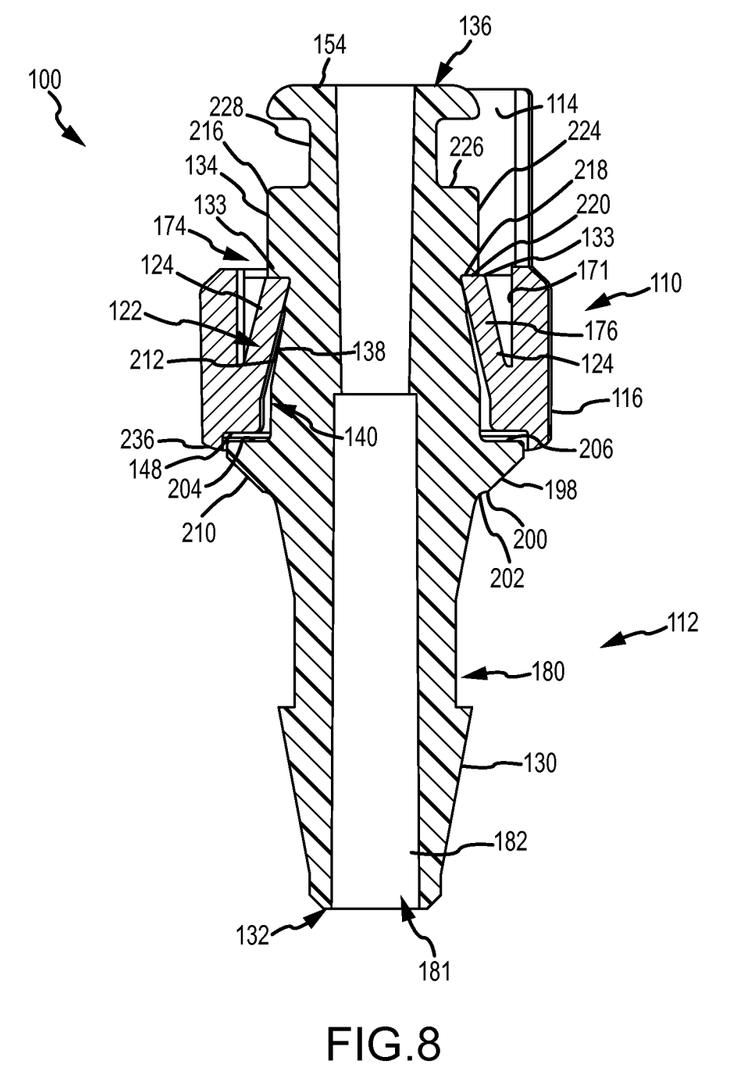
FIG. 8 is a cross-section view of the connector assembly taken along line 8-8 as shown in FIG. 4.
Figure 9:
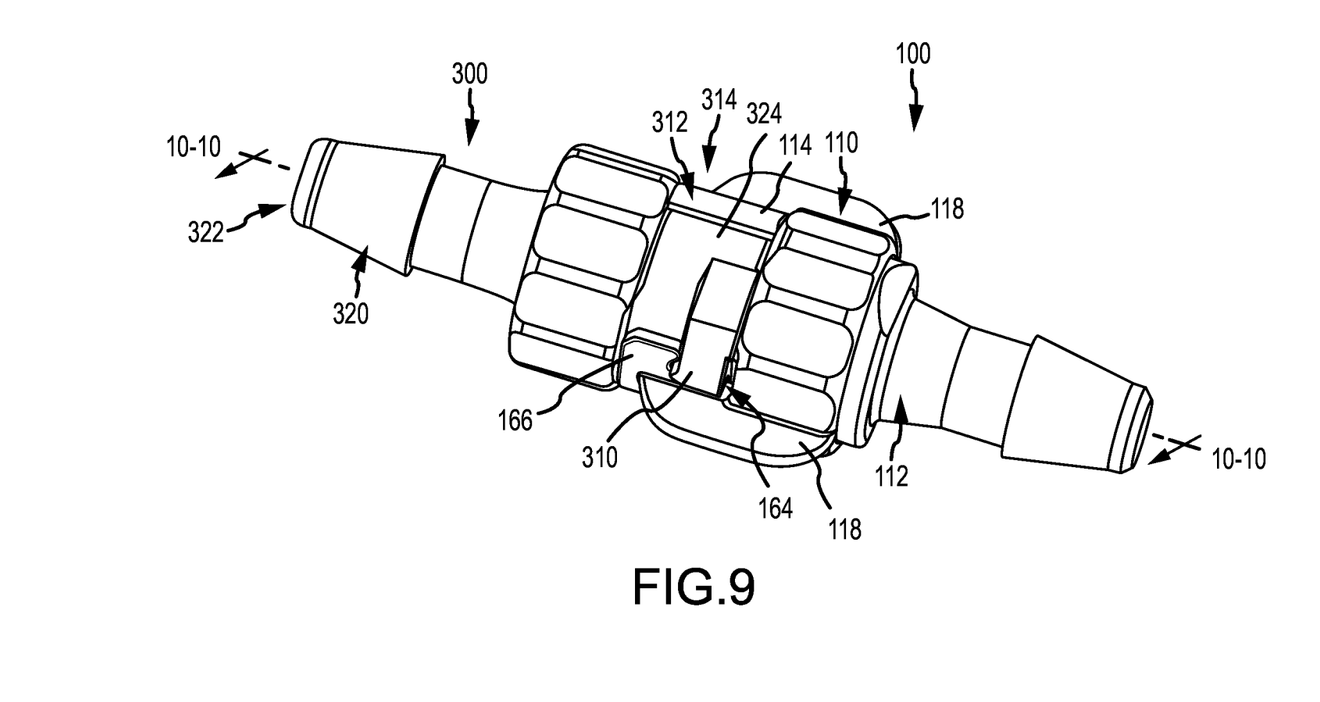
FIG. 9 is an isometric view of an implementation of the connector assembly of FIG. 1 joined to a female mating connector.

Referring to the latch member 110 of the connector assembly 100 shown in FIGS. 1-6 and 8-10, the latch walls 114 of the latch member 110 may be configured to join to a female connector member 300 at a mating latch 310 of the female connector member 300 (see, e.g., FIG. 9). The latch walls 114 may longitudinally depend outward from a circumferential edge 150 and may extend a distance such that, in the assembled position of the connector assembly 100 in FIGS. 1-4 and 7, terminal edges 152 of the latch walls 114 are in approximately the same plane as the terminal end surface 154 of the second end 136 of the connector member 112. As best shown in FIGS. 5-6, the latch walls 114 may form an arcuate shape as the latch walls 114 extend around portions of the circumferential edge 150 in arcs of about 90 degrees. A first lateral end 158 of each latch wall 114 may form a planar edge 156 and a second lateral end 162 opposite the first lateral end 158 may be formed as a notched sidewall 160. The planar edge 156 maybe configured to enable the mating latch 310 of the female connector member 300 to slide along the planar edge 156 as the female connector member 300 is positioned on the connector assembly 100, as described below.

The notched sidewall 160 may define a latch recess 164 and form a generally hook-shaped latch arm 166 in the latch wall 114. The upper edge surface 150 of the annular collar 116 may define and indentation 151 under the latch arm 166 adjacent the notched sidewall 160 in order to provide clearance for the mating latch 310 of the female connector member 300. An angled portion of the notched sidewall 160 may define a lower portion of a latch arm 166 and the terminal edge 152 of the latch wall 114 may define an upper portion of the latch arm 166. Proximate the free end of the latch arm 166, a latch protrusion 168 may extend toward an upper edge surface 150 of the annular collar 116. The latch protrusion 168 may thereby define a notch 169 in the latch arm 166. The latch arm 166 and the notched sidewall 160 defining the latch recess 164 may be configured with a shape complementary to the mating latch 310 of the female connector member 300 to enable latching between the connector assembly 100 and a female connector member 300, described below.

The outer surface 120 of the annular collar 116 may be knurled in the form of a number of grip protrusions 170 separated by grip indentations 171. The grip indentations 171 and grip protrusions 170 of the latch member may facilitate a user's grip on the latch member 110 and may add some strength and rigidity to the latch member 110.

Figures 3, 4:
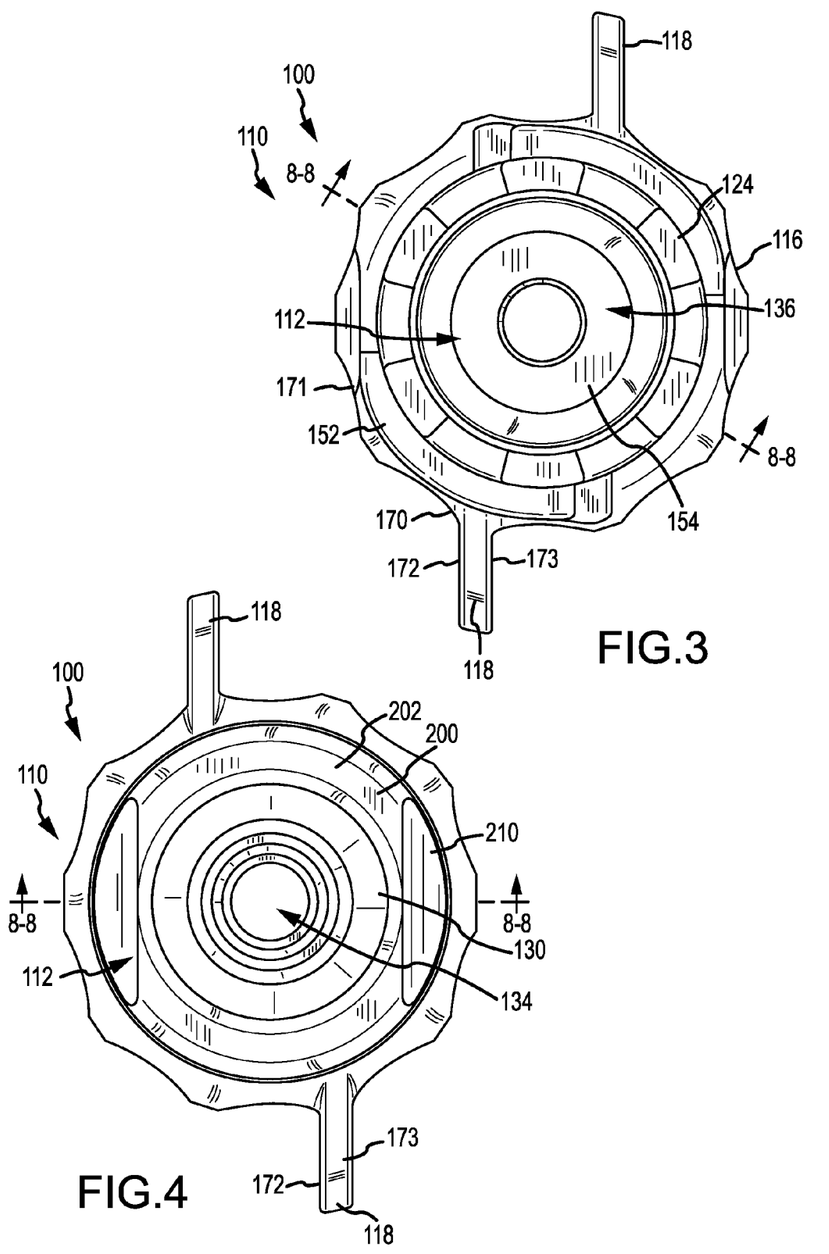
FIG. 3 is a top plan view of the connector assembly of FIG. 1.
FIG. 4 is a bottom plan view of the connector assembly of FIG. 1.

The wing grips 118 of the latch member 110 may form wing-like protrusions extending from the exterior surface 146 of the latch walls 114, the outer surface 120 of the annular collar 116, or both as shown in the figures. The pair of wing grips 118 may extend from the outer surface 120 of the annular collar 116 and the latch wall 114 at an angle slightly offset from normal such that the wing grips 118 do not extend radially from the latch member 110. As show in FIGS. 3 and 4, the wing grips 118 extend in planes that are parallel to, but offset from the longitudinal axis of both the annular collar 112 and the entire connector assembly 100. In some implementations, the wing grips 118 may extend along the exterior surface 146 of the latch wall 114 immediately adjacent the latch recess 164 and the latch arm 166. In some implementations, the wing grips 118 may extend outwardly as extensions of the grip protrusions 170 as best shown in FIG. 3. In addition or alternatively, the wing grips 118 may extend outwardly from the grip indentations 171. While FIGS. 1-5 and 9 show two wing grips 118 extending from the exterior of the annular collar 116, the latch member 110 may include additional wing grips 118 extending from the annular collar 116 as desired.

The wing grips 118 may provide contact surfaces for a user's fingers. For example, each wing grip 118 may define a first surface 172 and a second surface 173, and the first and second surfaces 172, 173 may be configured to receive pressure by a user's fingers or palm to facilitate relative rotation between the latch member 110 and the connector member 112 to enable the connector assembly 100 to join to the female connector member 300 (see FIG. 12). Without the wing grips 116, due to the small size of the latch member 110, the user would have to exert a significant amount of force on the latch member 110 to prevent it from slipping in the user's fingers during rotation. In addition, the wing grips 118 may facilitate assembly of the latch member 110 and the connector member 112 before joining the connector assembly 100 to a female connector member 300.

In some implementations, the wing grips 118 may be configured to reinforce the latch wall 118 in an area proximate the latch arm 166. For example, as best shown in FIGS. 5A and 5B, the wing grips 118 may be joined to the latch wall 114 in an area adjacent to the latch arm 166 and may add rigidity to the latch wall 114 and to the latch arm 166 of the latch wall 114. This arrangement may help maintain the connection between the connector assembly 100 and a female connector member 300 under high rotational forces, or axial tension loads exerted on the combined connector. For example, with typical collar-type connectors, high axial tension causes the latch arm 166 to flare radially outward whereby the latch protrusion 168 may lose engagement with the mating latch 310 or even cause the latch arm 166 to shear off. However, in the implementations of rotatable latch members 110 with wing grips 118 as disclosed herein, the location and configuration of the wing grips 118 reinforce the latch arm 166 and instead may cause the latch protrusion 168 to flex radially inward towards a longitudinal axis of the connector assembly 100 under an axial tension load. The wing grips 118 thereby cause the latch protrusion 168 and the latch arm 166 to "dig in" to the mating latch 310 of the mating connector member under an axial tension load 300 to help prevent disengagement.

A number of snap arms 124 may form a snap assembly 122 about an interior surface 121 of the annular collar 116 of the latch member 110 the snap arms 124 may be configured to join the rotatable latch member 110 to the connector member 112 as further described below. The annular collar 116 with the snap arms 124 may be considered similar to a collet. However, while the snap assembly 122 connects the latch member 110 to the male connector member 112, unlike a collet, the snap assembly 122 does not tightly compress around the male latch member 112 and the latch member is free to rotate around the male connector member 112. The snap arms 124 may be integrally formed with the inner surface 121 of the annular collar 116 at a first open end 148 of the annular collar 116 and may freely project from the interior surface 121 at an angle of extension in a direction toward both the longitudinal axis of the connector assembly 100 and the second open end 174. The freely projecting portion 176 of the snap arms 124 may be configured with a surface having a substantially flat or planar central region and tapered side regions with a rounded or beveled shape for interfacing with the connector member 112.

A lateral cross-section of the freely projecting portions 176 of the snap arms 124 may be likened to a D-shape with the curved side facing radially outward. The freely projecting portions 176 of the snap arms 124 may taper along their length as the snap arms 124 extend in the direction of the second open end 174. The snap arms 124 may terminate in free ends 133 proximate the second open end 174. The free ends 133 of the snap arms 124 may include a terminal end surface 178 configured with a rounded or beveled shape. The snap arms 124 may be configured to enable insertion of the connector member 112 into the latch member 110 from the first open end 140 towards the second open end 174 and may substantially prevent the connector member 112 from detaching from the latch member 110 upon reaching the assembled position of the connector assembly 100 of FIGS. 1-4.

Referring to FIGS. 1-4 and 7, the connector member 112 may be formed of a connector body 180 configured as a generally elongated member with a lumen 181 defined by an internal wall 182 extending from the barbed end 132 to the male insert end 136. The internal wall 182 may define the cylindrical lumen 181 having a diameter that is substantially uniform or may form a lumen having a conical shape with a tapering diameter, or both. At the barbed end 132, a barb connector portion 130 may be configured to receive tubing from a blood pressure cuff or a blood pressure measurement device (not shown). At the male insert end 136, the male connector portion 134 may be configured for receiving the female connector member 300 as described below. Between the ends 132, 136 of the connector member 112, an engagement portion 138 may be configured for receiving the snap assembly 122 of the latch member 110.

The barb connector portion 130 of the connector member 112 may be configured with a radiused or beveled portion 184 proximate the first (barbed) end 132 that leads to a cylindrical portion 186 extending distally away from the first (barbed) end 132, and a conical portion 188 flaring outwardly from the cylindrical portion 186 and at an angle relative to the longitudinal axis of the connector assembly 100. A second cylindrical portion 192 of the connector body 180 may extend distally from the distal end of the conical portion 188. The second cylindrical portion 192 is of a smaller diameter than the diameter of the distal end of the conical portion 188, thereby forming an annular flange 190 at the interface between the conical portion 188 and the second cylindrical portion 192, thereby forming a barb shape. The conical portion 188 of the barb connector portion 130 may be elongated relative to the beveled and cylindrical portions 184, 186 of the barb connector portion 130.

FIGS. 1-4 and 7 show only one configuration of the barb connector portion 130, but the barb connector portion 130 may have various configurations, as would be understood by those skilled in the art. In some implementations, the angle at which the conical portion 188 of the barb connector portion 130 flares, as well as the radius of the conical portion 188 proximate the flange 190, may vary, for example, depending on the size of tubing to be received by the barb connector portion 130. The second cylindrical portion 192 of the connector body 112 may extend toward the male insert end 136 parallel to the longitudinal axis and may transition to a flared portion 194 extending outwardly and at an angle relative to the longitudinal axis.

An annular protrusion 198 may separate the flared portion 194 of the connector body 112 from the engagement portion 138 of the connector member 112. The annular protrusion 198 may project radially outward relative to the flared portion 194 and the male connector portion 134 of the connector member 112 to reach an outer diameter that is larger than an inner diameter at the inner surface 121 of the annular collar 116 of the latch member 110 to provide an abutting contact between the annular protrusion 198 and the latch member 110 upon assembly. A first surface 200 of the annular protrusion 198 of the connector member 112 facing the barbed end 132 may be configured as a tube stop 202. For example, when rubber tubing is placed over the barb connector portion 130 and slides towards the male insert end 136, the first surface 200 of the annular protrusion 198 may serve to stop the rubber tubing from further travel along the length of the connector member 112. A second surface 204 of the annular protrusion 198 may face the male insert end 136 and may be configured as a stop 206 for abutting with a surface of the latch member 110 during assembly. A sidewall 208 of the annular protrusion separates the first and second surfaces 200, 204 of the annular protrusion 198 and may include one or more grip surfaces 210 configured for gripping by a user's fingers, for example, during assembly of the latch member 110 with the connector member 112.

The latch member 110 may be assembled with the male connector member 112 in a reverse direction compared to a typical direction of assembly (e.g., from a barb connector side of a connector member). As best shown in FIGS. 7 and 8, the engagement portion 138 of the connector member 112 may be configured to receive the latch member 110 and may extend from the second surface 204 of the annular protrusion 198 in the direction of the male insert end 136 up to an annular collar 216. Proximate the annular protrusion 198 of the connector member 112, the engagement portion 138 may form a conical section 212 with a tapering circumference extending at an angle towards the longitudinal axis. The conical section 212 may be separated from each of the annular protrusion 198 and the annular collar 216 by cylindrical sections 214. The angle of taper of the conical section 212 may be generally complementary to the angle of extension of the snap arms 124 of the snap assembly 122 of the latch member 110, as described further below.

From the conical section 212 or the cylindrical section 214, as the male connector portion 134 extends towards the male insert end 136, the annular collar 216 may project radially from the male connector portion 134. The annular collar 216 may define a first surface 218 facing the barbed end 132 and configured to abut with the free ends 133 of the snap arms 124 of the latch member 110. The annular collar 216 may thereby form an annular stop surface 220 configured to interface with the free ends 133 of the snap arms 124 and to prevent the snap arms 124 from moving in the direction of the male insert end 136. A longitudinal distance between the annular protrusion 198 and the annular collar 216 may be selected to be slightly longer than the length of the snap arms 124 of the latch member 110. In some implementations, the surfaces of the engagement portion 138 may be substantially uniform or smooth to facilitate free rotation of the latch member 110 about the connector member 112.

An annular recess 228 of the male connector portion 134 of the connector member 112 may extend from a second surface 226 of the annular collar 216 in the direction of the male insert end 136. The annular recess 228 may be configured to receive a seal member 230 such as an O-annular collar or a cup seal that may facilitate providing a seal between the connector assembly 100 and a female connector member 300. The outer diameter of the male connector portion 134 may further be selected to be received within an internal diameter of the female portion 312 of the female connector member 300, described below in connection with FIGS. 9 and 10.

Referring to FIG. 8, a cross-sectional view of the connector assembly 100 in the assembled position of FIGS. 1-4 is shown. In FIG. 8, the latch member 110 of the connector assembly 100 may engage with the connector member 112 at the engagement portion 138 of the connector member 112. An annular gap 140 may be formed between the engagement portion 138 and the snap arms 124 of the snap assembly 122 of the latch member 110 from the annular protrusion 198 to a point along the engagement portion 138 at which the free ends 133 of the strap arms 124 engage the engagement portion 138. The annular protrusion 198 and the annular collar 216 of the connector member 112 each may extend radially outwardly from the connector member 112 by distances that are slightly larger than the inner diameter of the snap assembly 122 at each of the first and second open ends 148, 174, respectively. For example, the annular collar 216 may extend radially outwardly by a distance so that the outer diameter of the annular collar 216 is slightly larger than an inner diameter defined by the free ends 133 of the snap arms 124 of the snap assembly 122 at the second open end 174 of the latch member 110. The first surface 218 of the annular collar 216 of the connector member 112 may thereby form a first snap assembly stop 220. The annular protrusion 198 of the connector member 112 may extend radially outwardly by a distance so that the outer diameter of the annular protrusion 198 is slightly larger than an inner diameter of the latch member 110 that may be defined by the portion of the snap assembly 122 joined to the inner surface 121 of the annular collar 116 at the first open end 148. The second surface 204 of the annular protrusion 198 may form a second snap assembly stop surface 206.

As the male insert end 136 of the connector member 112 is inserted into the first open end 148 of the latch member 110, the male insert portion 134 of the connector member 112 may pass through the snap assembly 122 and the annular collar 216 of the connector member 112 may force the snap arms 124 of the latch member 110 to flex radially outwardly or toward the inner surface 121 of the latch member 110. As the male insert portion 134 of the connector member 112 exits the snap assembly 122 via the second open end 174, the snap arms 124 of the snap assembly 122 may clear sidewall 224 of the annular collar 216 and may snap back radially inward toward the engagement portion 138 of the connector member 112. The free ends 133 of the snap arms 124 may thereby slip under and engage with the first stop surface 220 of the annular collar 216 of the connector member 112. At the same time, the second stop surface 206 of the annular protrusion 198 of the connector member 112 may abut the portion of the snap assembly 122 joined to the inner surface 121, adjacent a lower terminal end surface 236 of the latch member 110.

While the connector member 112 is disclosed as including a male connector portion 134 at the male insert end 136 for insertion into the first open end 148 of the latch member 110, the connector member 112 may be configured with any type of connector portion at the male insert end 136 that may be inserted into the first open end 148 of the latch member 110 in the manner described above.

In the assembled position of the connector assembly 100, the latch member 110 and the connector member 112 may freely rotate relative to one another about the longitudinal axis due to the snap assembly 122 of the latch member 110 being seated about the engagement portion 138 of the connector member 112. In some implementations, the surfaces of the snap assembly 122 and the engagement portion 138 that contact one another may be substantially smooth or may be configured with surfaces that facilitate free rotation of the connector assembly 100. The configuration of the snap arms 124 of the snap assembly 122 and/or arrangement of the latch member 110 relative to the engagement portion 138 of the connector member 112 may provide strength to the snap assembly 122 and the engagement portion 138, and further between the components of the connector assembly 100.

By providing a connector assembly 100 configured to be assembled by inserting the male insert end 136 of a male connector member 112 (rather than the barbed end 132) into the first open end 148 of the rotatable latch member, the configuration of the barbed connector portion 130 of the connector member 112 may be selected based on its intended use as opposed to based on an ability to insert the barbed connector portion 130 through the latch member 110 (e.g., via the second open end 174) and past the snap assembly 122 of the latch member 110. This may enable the barb connector portion 130 to have a larger outer diameter than the inner diameter of the latch member 110. While the connector member 112 is shown with a barb connector portion 130 at the first (barbed) end 132, a variety of connector portions may be provided at the first end 132 due to the fact that the configuration of the first end 132 does not affect the assembly process of the above-described connector assembly 100.

In addition, because the configuration of the annular protrusion 198 of the connector member 112 may provide an outer diameter that is larger than an inner diameter of the latch member 110, the annular protrusion 198 may provide both the tube stop 202 for the barb connector portion 130 of the connector member 112 and the second stop surface 206 for receiving the latch member 110, as described above. Because tubing (not shown) assembled on the barb connector portion 130 of the connector member 112 may be prevented from traveling past the annular protrusion 198 of the connector member 112 forming the tube stop 202, the tubing may be separated from the latch member 110, which may enable the latch member 110 to rotate freely around the engagement portion 138 of the connector member 112 without interference from the tubing. This is unlike prior art two-piece connectors assembled by passing the end having the barb connector portion (e.g., barb connector portion 130) through the second open end of a collar member because any tube stop associated with a barb connector portion in such a configuration requires an outer diameter that is smaller than an inner diameter of the collar member.

Figure 10:
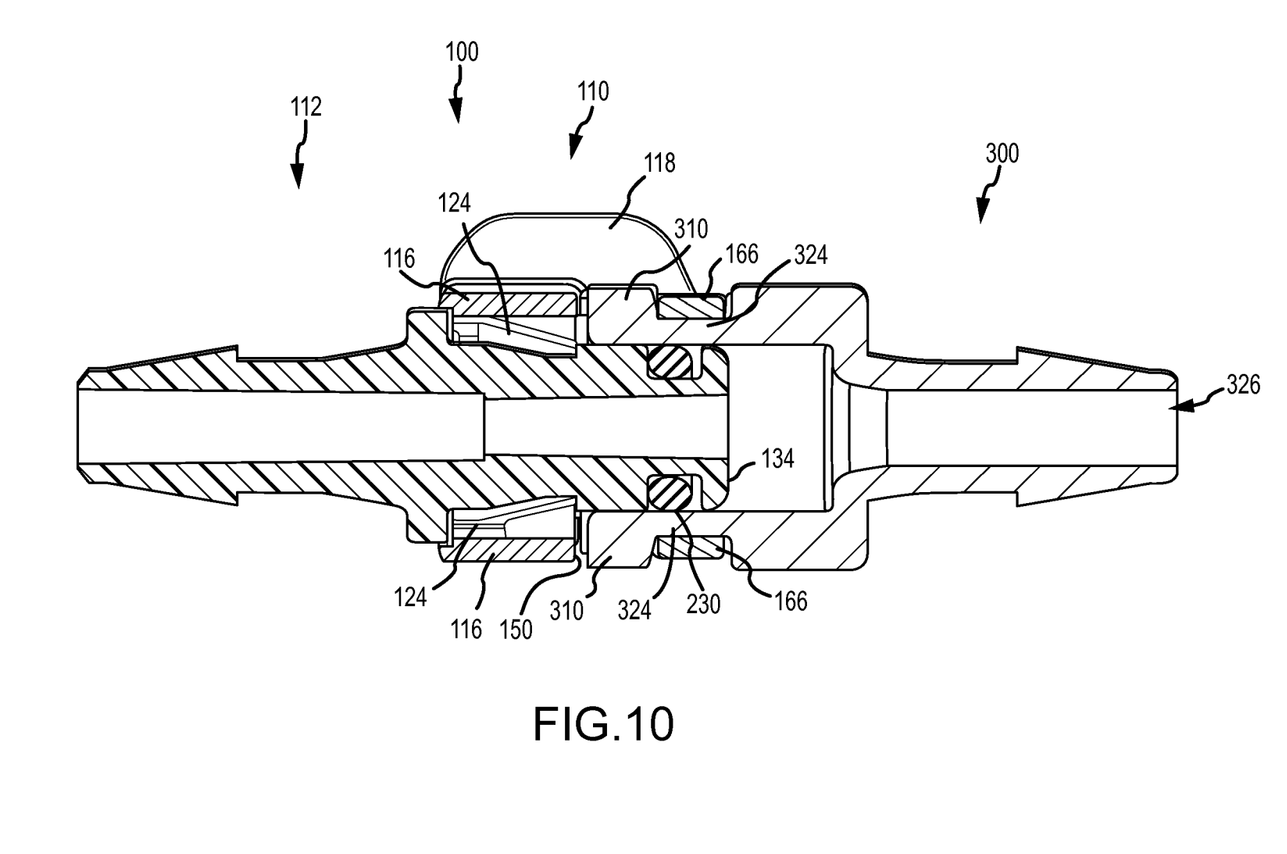
FIG. 10 is a cross-section view of the connector assembly and female mating connector of FIG. 9 taken along line 10-10 as shown in FIG. 9.

Referring to FIGS. 9-10, an isometric view and a cross-sectional view are shown of the connector assembly 100 of FIG. 1 joined to a female connector member 300. The female connector member 300 may be configured with a mating latch 310 extending from a female connector portion 312 at a first end 314 and a barb connector portion 320 portion at a second end 322. The female connector portion 312 of the female connector member 300 may be configured to receive the male insert portion 134 of the male connector member 112 of the connector assembly 100. In some implementations, a seal member 230 provided on the male insert portion 134 of the connector member 112 may engage with the inner diameter of a sidewall 324 defining a lumen 326 of the female connector member 300 to provide sealing between the male connector member 112 and the female connector member 300.

The mating latch 310 of the female connector portion 312 of the female connector member 300 may be configured to latch with the latch arm 166 and latch protrusion 168 of the latch member 110. For example, the female connector portion 312 of the female connector member 300 may be inserted over the male insert portion 134 of the connector member 112 and the mating latch 310 may slide along the planar edge 156 of one latch wall 114 until the female connector portion 312 abuts the upper edge surface 150 of the annular collar 110. In some implementations, a distance between the latch wall 114 of the latch member 110 and the male connector portion 134 of the connector member 112 may substantially correspond to a thickness of a portion of the sidewall 324 of the female connector portion 320. The mating latch 310 may project beyond the outer surface of the sidewall 324 thereby preventing the mating latch 310 and the underlying area of the sidewall 324 from passing between the latch wall 114 and the male connector portion 134. In this case, the user may align the mating latches 310 of the female connector member 300 with the latch member 110 in an area between the planar sidewall 156 of one latch wall 114 and the latch arm 166 of a second latch wall 114 and then may slide the female connector portion 312 of the female connector member 300 over the male connector portion 134 of the connector member 312. Upon the female connector portion 312 abutting the upper edge surface 150, the mating latch 310 of the female connector member 300 will be positioned adjacent the latch recess 164 of the latch member 110 in an unlatched position.

A user may rotate the latch member 110 relative to the connector member 112 and the female connector member 300 via the reverse wing grips 118 of the latch member 110 so that the mating latch 310 of the female connector member 300 is inserted into the latch recess 164. The mating latch 310 may be formed with a bump or protrusion and notch corresponding to the latch protrusion 168 and notch 169 of the latch arm 166. The latch protrusion 168 of the latch arm 166 of the latch member 110 may slide past the corresponding protrusion on the mating latch 310 and come to rest in the notch on the mating latch. Similarly, the protrusion on the mating latch 310 may slide past the protrusion 168 on the latch arm 166 and come to rest in the notch 169. The indentation 151 in the upper edge surface 150 of the annular collar 116 provides additional clearance for the mating latch 310 to move past the latch arm 166 and the protrusion 168. Thus, upon rotation of the latch member 110 with respect to the female connector member 300, the connector member 112 and female connector member 300 become locked together in the position shown in FIGS. 9 and 10.

Accordingly, rotation of the latch member 110 relative to the connector member 112 and female connector member 300, in one direction, may latch the connector assembly 100 to the female connector member 300, and rotation in a second direction opposite the first direction, may unlatch the connector assembly 100 from the female connector member 300. The degree of rotation for latching and unlatching the connector assembly 100 and mating connector 300 may be by a partial revolution, such as a quarter turn, a one-third turn, a half turn, and the like. Due to the latching occurring as a result of the relative rotation or twisting of the latch member 110 and the mating latch 310, the connector assembly 100 may be referred to as a twist lock connector assembly. Further, upon placement under an axial tension load, the reinforcement of the latch wall adjacent the latch arms 166 causes the latch arms 166 and latch protrusion 168 to flex radially inwardly towards the mating connector 300 and may "dig in" to the mating latch 310 to strengthen the latched engagement under the load rather than allowing a radially outward flex that would promote disengagement of the latch member 118 from the female connector member 300 and failure of the connection.

Once the latch member 110 is connected to the female connector member 300, the two components are rotationally locked with respect to each other. However, the latch member 110 may still freely rotate about the engagement portion 138 of the male connector member 112. Thus, once two sections of tubing are respectively connected to the barbed end 132 of the male connector member 112 and the barbed connector portion 320 of the female connector member 300, the combined connector assembly 100 and female connector member 300 can provide for relative rotation between the sections of tubing and there by reduce the possibility of twisting or binding of the fluid tubing when connected, which could negatively impact fluid flow therethrough.

The latch member 110 and male connector member 112 of the connector assembly 100, as well as the female connector member 300, may each be integrally formed for example, by injection molding and overmolding processes or may be formed of multiple components joined by any suitable fastening mechanism. The components may be formed of materials that provide strength and rigidity to their respective components, while providing some flexibility to enable to the components to flex under tension loads. For example, the components of the connector assembly 100 may be formed of polymer resins, such as polypropylene, and the polymer resin may be chemical resistant and may withstand multiple sterilization processes.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. In particular, it should be understood that the described technology may be employed independent of a personal computer. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A connector assembly, comprising:
   a latch member, comprising:
      an annular collar with a first open end, a second open end, and a terminal end, the first open end opposing the second open end in a longitudinal direction, and the terminal end extending from the first open end in the longitudinal direction away from the second open end;
      an arcuate latch wall extending from a circumferential edge of the annular collar and defining a latch recess and a latch arm within the latch wall;
      a wing grip extending outwardly from an exterior surface of the latch wall adjacent the latch recess to define an angle between the wing grip and the exterior surface of the latch wall and configured to reinforce the latch arm by countering a tendency of the latch arm to flex radially outward when the connector assembly is subject to a tension load along a longitudinal axis of the connector assembly; and
      at least one snap arm having a free end extending from the first open end toward the second open end; and
   a connector member configured to receive and retain the latch member about an outer surface thereof, the connector member comprising:
      an annular protrusion having a first surface, a second surface, and a sidewall, the first surface and the second surface projecting radially outward from the outer surface of the connector member, the sidewall separating the first surface and the second surface, wherein
      when the latch member is retained on the connector member the annular protrusion is at least partially contained within the annular collar, such that the terminal end of the annular collar is positioned radially about the sidewall of the annular protrusion.

2. The connector assembly of claim 1, wherein the wing grip extends outwardly along both the annular collar and the arcuate latch.

3. The connector assembly of claim 1, wherein the wing grip defines a plane that is parallel to, but offset from, the longitudinal axis of the connector assembly.

4. The connector assembly of claim 1, wherein when the connector assembly is placed under a tension load exerted along the longitudinal axis of the connector assembly, the wing grip causes the latch arm to flex radially inward toward the longitudinal axis of the connector assembly.

5. The connector assembly of claim 1, wherein the connector member is a male connector configured to be received in a lumen of a corresponding female connector member.

6. The connector assembly of claim 5, wherein
   the male connector comprises a first end configured for connection with a length of fluid tubing and a second end configured for insertion into a female connector; and
   the second end is configured for insertion through the annular collar and defines the outer surface upon which the latch member is received and retained.

7. A connector assembly, comprising:
   a latch member, comprising:
      an annular collar with a first open end, a second open end, and a terminal end, the first open end opposing the second open end in a longitudinal direction, and the terminal end extending from the first open end in the longitudinal direction away from the second open end; and
      a snap assembly provided on an interior surface of the annular collar adjacent the first open end, the snap assembly comprising a plurality of snap arms arranged about a circumference of the interior surface of the annular collar, wherein each of the snaps arms is configured with a free end extending at an angle toward both a longitudinal axis of the annular collar and the second open end; and
   a connector member, comprising:
      a first end for attachment to a length of fluid tubing and a second end for connection with a complementary connector;
      a lumen defined by an internal wall of the connector member extending between the first end and the second end along a longitudinal axis of the connector assembly; and
      an engagement portion located adjacent the second end separated from the first end by an annular protrusion on an outer wall of the connector member having a diameter that is larger than a diameter of the first open end of the annular collar,
   wherein the latch member is rotatably connected with the connector member by insertion of the second end of the connector member into the first open end of the annular collar of the latch member until the first open end of the annular collar abuts the annular protrusion and, in the assembled position, the snap assembly of the latch member retains the latch member about the engagement portion of the connector member and the annular protrusion is at least partially contained within the annular collar, such that the terminal end of the annular collar is positioned radially about the annular protrusion.

8. The connector assembly of claim 7, wherein
   the engagement portion defines an annular flange,
   the annular flange is separated from the annular protrusion by a distance corresponding to a length of the snap arms, and
   a distal end of the snap arms abuts the annular flange, which prevents axial movement of the latch member toward the second end of the connector member.

9. The connector assembly of claim 7, wherein a surface of the engagement portion that interfaces with the snap assembly when the connector member and the latch member are joined in the assembled position is substantially smooth and enables the free rotation of the latch member and the connector member relative to one another.

10. The connector assembly of claim 7, wherein the latch member comprises at least one wing grip extending outwardly from an exterior surface of the annular collar, wherein the at least one wing grip is configured to be gripped by a user to enable the latch member and the connector member to rotate relative to one another.

11. The connector assembly of claim 10, wherein the latch member further comprises
  an arcuate latch wall extending from a circumferential edge of the annular collar and defining a latch recess and a latch arm within the latch wall; and wherein
  the wing grip further extends outwardly from an exterior surface of the latch wall adjacent the latch recess to define an angle between the wing grip and the exterior surface of the latch wall and is configured to reinforce the latch arm by countering a tendency of the latch arm to flex radially outward when the connector assembly is subject to a tension load along a longitudinal axis of the connector assembly.

12. The connector assembly of claim 11, wherein the wing grip defines a plane that is parallel to, but offset from, the longitudinal axis of the connector assembly.

13. The connector assembly of claim 11, wherein when the connector assembly is placed under a tension load exerted along the longitudinal axis of the connector assembly, the wing grip causes the latch arm to flex radially inward toward the longitudinal axis of the connector assembly.

14. The connector assembly of claim 7, wherein the first end of the connector member defines a barbed connector portion.

15. The connector assembly of claim 7, wherein the second end of the connector member defines a male insertion portion.

16. The connector assembly of claim 7, wherein the free ends of each of the snap arms extend at an angle towards the longitudinal axis in an initial position.

17. The connector assembly of claim 16, wherein the snap arms are configured to flex from the initial position radially outward and away from the longitudinal axis upon insertion of the second end of the connector member into the first open end of the latch member.

18. The connector assembly of claim 17, wherein the snap arms are biased toward the initial position upon the latch member and the connector member reaching an assembled position.

19. The connector assembly of claim 7, wherein the annular protrusion comprises a surface facing the first end of the connector member and is configured as a tube stop for preventing a fluid tube from passing beyond the tube stop toward the second end of the connector member.

\* \* \* \* \*